United States Patent [19]

Kusano et al.

[11] Patent Number: 4,595,364

[45] Date of Patent: Jun. 17, 1986

[54] DENTAL PROSTHESIS AND PROCESS FOR PREPARING THE SAME

[75] Inventors: Takae Kusano; Masato Ueno, both of Hiroshima, Japan

[73] Assignees: Molten Corp.; Kabushiki Kaisha Four Brain, both of Hiroshima, Japan

[21] Appl. No.: 701,006

[22] Filed: Feb. 12, 1985

[30] Foreign Application Priority Data

Feb. 15, 1984 [JP] Japan ................................ 59-27866
Jun. 15, 1984 [JP] Japan ............................... 59-124230
Jun. 15, 1984 [JP] Japan ............................... 59-124231

[51] Int. Cl.$^4$ .............................................. A61C 13/24
[52] U.S. Cl. ..................................... 433/185; 433/188
[58] Field of Search ............... 433/185, 184, 188, 167, 433/168

[56] References Cited

U.S. PATENT DOCUMENTS

| | | | |
|---|---|---|---|
| 1,887,970 | 11/1932 | Valbuena | 433/185 |
| 3,555,683 | 1/1971 | Gregorovic et al. | 433/185 |
| 4,024,636 | 5/1977 | Colpitts et al. | 433/167 |

FOREIGN PATENT DOCUMENTS

| | | | |
|---|---|---|---|
| 111661 | 12/1928 | Austria | 433/184 |
| 28800 | 11/1921 | Denmark | 433/188 |
| 186363 | 10/1955 | Fed. Rep. of Germany | 433/184 |
| 585502 | 11/1958 | Italy | 433/184 |

Primary Examiner—John J. Wilson
Attorney, Agent, or Firm—Armstrong, Nikaido, Marmelstein & Kubovcik

[57] ABSTRACT

A dental prosthesis having artificial teeth, a denture base made of a hard polymer material and an elastic lining layer provided on an inner surface of the denture base, comprising (a) a recess portion provided on the elastic lining layer for forming a sealed chamber, (b) a small bore for communicating the sealed chamber with an exterior, (c) a check valve member for exhausting air in the chamber from the recess portion to the exterior, and (d) a member for preventing an alveolar gingiva from projecting into the recess portion. The dental prosthesis can be stably and steadily supported on an alveolus ridge of a patient.

6 Claims, 34 Drawing Figures

FIG. 1
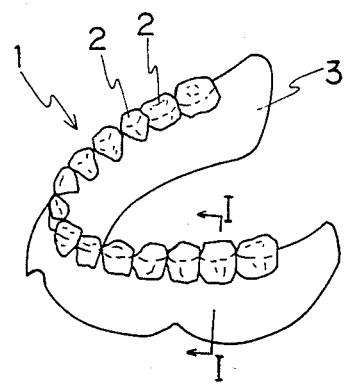
FIG. 2
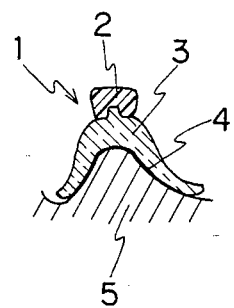
FIG. 3A  FIG. 3B  FIG. 4
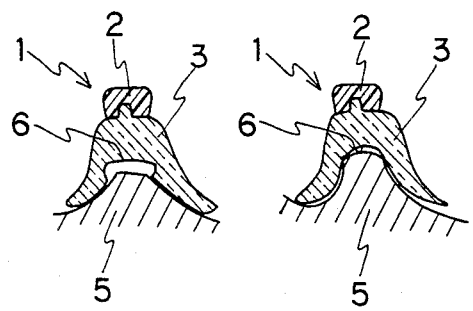 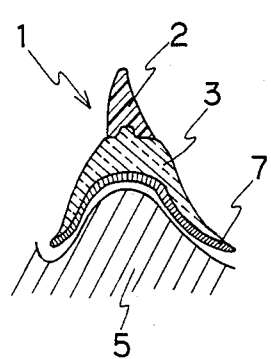
FIG. 5
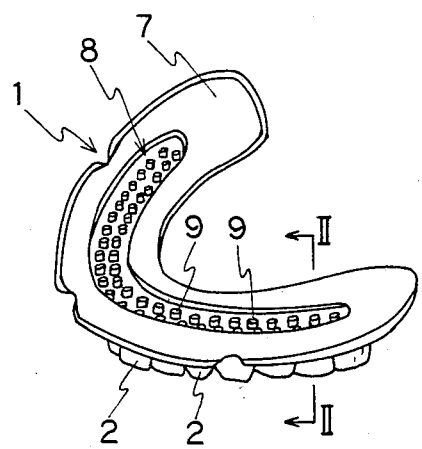
FIG. 6
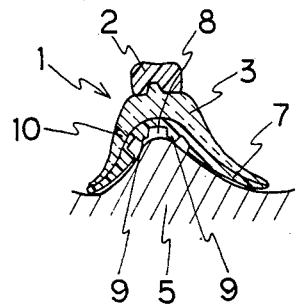

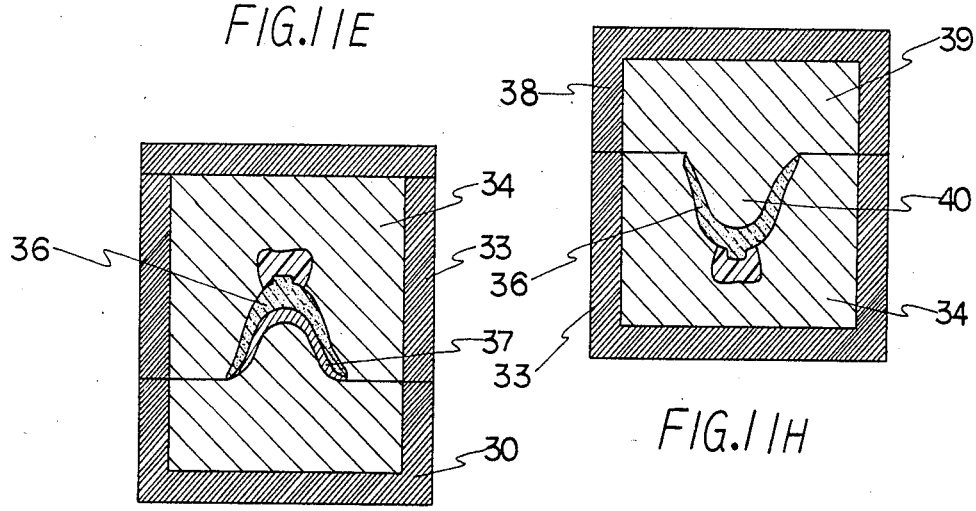
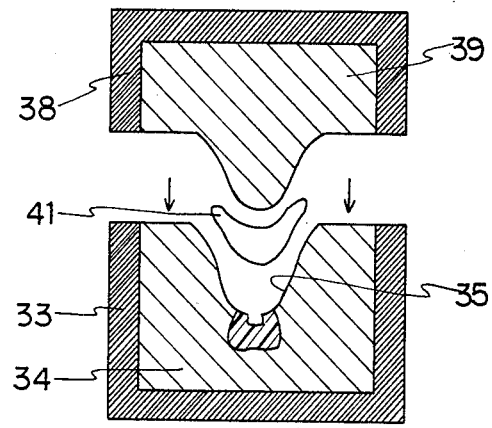
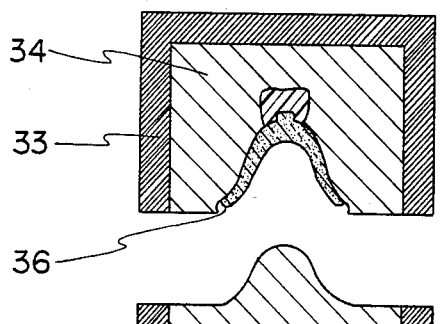
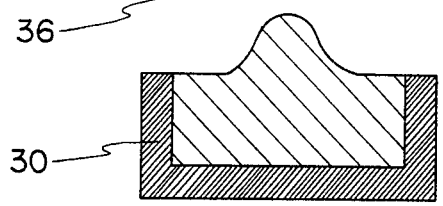
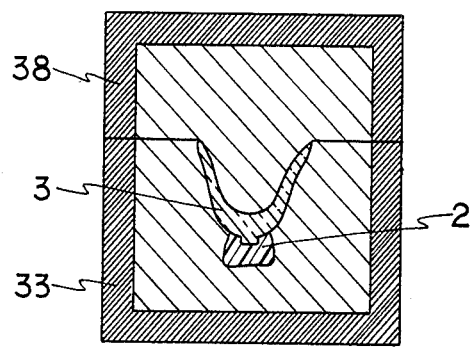

FIG. 12
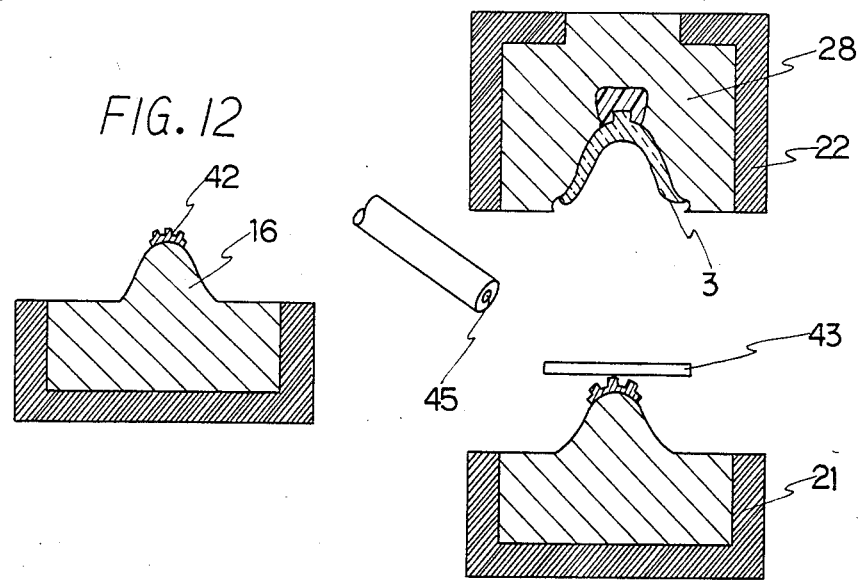
FIG. 14A
FIG. 13
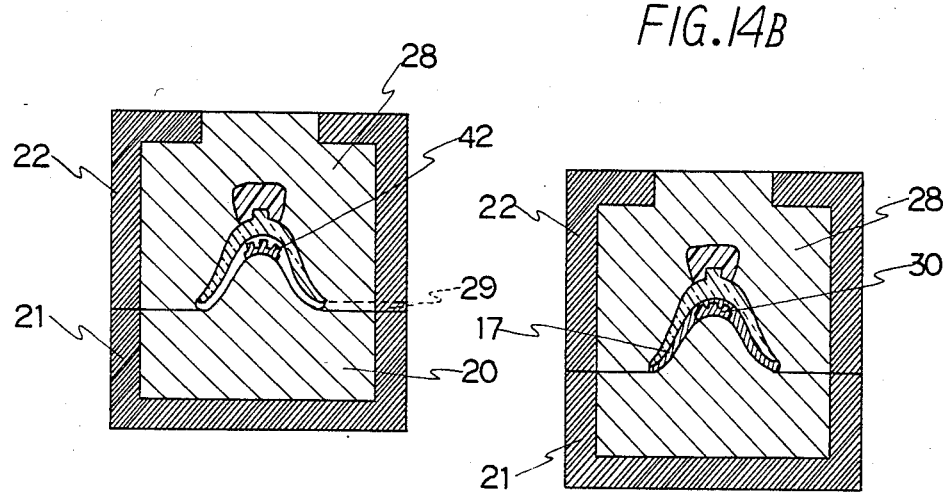
FIG. 14B

DENTAL PROSTHESIS AND PROCESS FOR PREPARING THE SAME

BACKGROUND OF THE INVENTION

The present invention relates to a dental prosthesis and a process for preparing the same, and, more particularly, to a dental prosthesis which can be stably and steadily supported on an alveolus ridge of a patient, and the process for preparing the same.

FIG. 1 shows a conventional dental prosthesis 1. The conventional dental prosthesis 1 comprises artificial teeth 2 and a denture base 3 holding the artificial teeth 2. As shown in FIG. 2 which is a sectional view taken along line I—I of FIG. 1, the denture base 3 has an inner surface 4 of inverted U-shape in section. At this inner surface the denture base 3 fits to mucosa of an alveolus ridge 5. Generally, the dental prosthesis 1 is constructed so that the dental prosthesis can be easily detached for the purpose of washing. However, the dental prosthesis 1 often comes off against user's will, or causes uncomfortable tenderness or pain due to slipping under mastication movement, because the dental prosthesis 1 has no particular fixing means.

To resolve the above problems, there is proposed another conventional dental prosthesis as shown in FIGS. 3A and 3B, where a recess portion 6 being provided on a bottom of the inverted U-shaped inner surface 4 of the dental prosthesis. According to such a construction, during the mastication, air within a chamber (FIG. 3A) defined by the recess portion 6 and the alveolus ridge 5 escapes through the surfaces between the denture base 3 and the mucosa of the alveolus ridge 5, so that pressure in the chamber is reduced. As a result, the dental prosthesis 1 is sucked to the alveolus ridge 5. However, when the dental prosthesis 1 is used for a long time, an alveolar gingiva deforms and projects into the recess 6 and occupies the chamber as shown in FIG. 3B. As a result, the effect of sucking is lost, which causes the dental prosthesis to come off.

FIG. 4 shows another conventional dental prosthesis. In such a dental prosthesis, in order that a fitting property to the alveolus ridge is improved and the tenderness is reduced, an elastic lining layer made of an elastic rubber material is provided on an inner surface of the denture base 3. The elastic lining layer is adhered with a commercially available adhesive or is mechanically or structually engaged with the denture base. However, such a structure cannot also prevents the dental presthesis from coming off from the alveolus ridge.

An object of the present invention is to provide a dental prosthesis which resolve the aforementioned disadvantages of the prior art. More particularly, an object of the present invention is to provide a dental prosthesis capable of being stably fitted and adapting to smoothly perform masticatory action.

SUMMARY OF THE INVENTION

In accordance with the present invention, there can be provided a dental prosthesis having artificial teeth, a denture base made of a hard polymer material for holding the artificial teeth and an elastic lining layer provided on an inner surface of the denture base, comprising (a) a recess portion provided on the elastic lining layer for forming a sealed chamber defined by the elastic lining layer and a mucosa of an alveolus ridge;
(b) a small bore for communicating the sealed chamber with an exterior through the elastic lining layer and the denture base;
(c) a check valve member inserted into the small bore for exhausting air in the chamber from the recess portion to the exterior; and
(d) a member for preventing an alveolar gingiva from projecting into the recess portion due to a deformation of the alveolar gingiva.

BRIEF DESCRIPTION OF THE DRAWINGS

FIG. 1 is a perspective view of a typical conventional dental prosthesis;

FIG. 2 is a sectional view taken along line I—I of FIG. 1;

FIGS. 3A and 3B are sectional views of another conventional dental prosthesis;

FIG. 4 is a sectional view of the other conventional dental prosthesis;

FIG. 5 is a perspective view from the bottom showing a first embodiment of a dental prosthesis of the present invention;

FIG. 6 is a sectional view taken along line II—II of FIG. 5;

FIGS. 11A to 11I are diagrams showing another procedures of step (2) of the process according to the present invention;

FIG. 12 is a sectional view for explanation of a procedure of step (3) of the process according to the present invention;

FIG. 13 is a sectional view for explanation of a procedure of step (4) of the process according to the present invention;

FIGS. 14A and 14B are sectional views for explanation of procedures of step (5) of the process according to the present invention.

DETAILED DESCRIPTION

FIGS. 5, 6, 7A and 7B show a first embodiment of a dental prosthesis of the present invention. FIG. 5 shows a structure of a back surface of the dental prosthesis 1 which is set on an alveolar part of mandible. Numeral 2, 3 and 7 indicate artificial teeth, a denture base and an elastic lining layer, respectively. The elastic lining layer 7 is provided on an inner surface of the denture base 3. The elastic lining layer is made of an elastic material such as a rubber or a synthetic resin. The elastic lining layer 7 is adhered or fused to the denture base 3. Numeral 8 indicates a recess portion provided on a bottom of a U-shaped portion of the elastic lining layer 7. Numeral 9 indicates a number of projections provided in the recess portion 8.

Figure 7A:
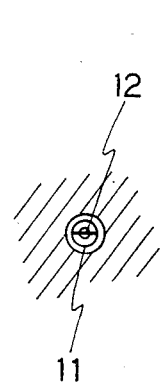
FIGS. 7A and 7B are a plan view and a sectional view of a check valve member in the present invention, respectively.
Figure 7B:
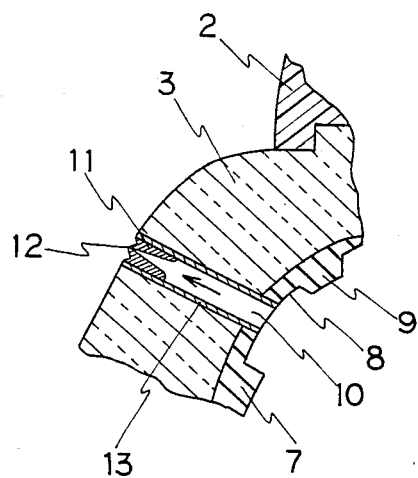

Numeral 10 indicates a small bore communicating the recess portion 8 with an exterior of the denture base 3, preferably at the side of a cheek, through the elastic lining layer 7 and the denture base 3. A diameter of the small bore 10 is about 1 to 5 mm. Numeral 11 indicates a check valve provided near an exit of the small bore 10. The check valve 11 is made of a soft elastic material such as a rubber. As shown in FIGS. 7A and 7B, the check valve 11 has a triangle section, and the top of the triangle apart from the denture base projects to a direction of the exterior surface of the denture base 3. The valve 11 is divided into two pieces along a diameter, i.e. a cutting line 12. Narrow bores in the form of point can be employed instead of the cutting line 12. Air or a saliva to be exhausted from the recess portion 8 pushes and opens the check valve 11, and is exhausted to the exterior through the cutting line 12. In case of the narrow bores, the air or saliva pushes and opens the narrow bores and is exhausted to an exterior through the narrow bores. The check valve 11 allows the air or saliva to pass from the recess portion 8 to the exterior of the denture base 3, i.e. in the direction of the arrow in FIG. 7B, but the check valve 11 prevents their counter flow, i.e. from the exterior of the denture base 3 to the recess portion 8. An outer surface of the check valve 11 is preferably shaped so as to have a gradually curved surface in order to clean in ease and to prevent dregs from sticking on the outer surface. Numeral 13 indicates a cylindrical body made of a synthetic resin, for example, the same material as the denture base. The cylindrical body 13 with the check valve 11 is inserted into the small bore 10.

The projections 9 provided in the recess porion 8 serves as a means for preventing an alveolar gingiva from projecting into the recess portion 8. A height of each projection 9 is equal to or lower than a distance between the bottom of the recess portion 8 and the mucosa of the alveolus ridge. Namely, the alveolar gingiva is sucked into a sealed chamber defined by the recess portion 8 and the alveolus ridge 5, since a mastication movement causes the inner pressure of the chamber to be reduced by exhausting the air in the chamber. In such a way, the alveolar gingiva tends to deform along a surface of the recess portion 8 and fill the recess portion 8, when the mastication is repeated for a long time. According to the present invention, however, since the projections 9 interferes with the filling of the alveolar gingiva, the recess portion 8 cannot be completely filled with the alveolar gingiva. Accordingly, the sucking operation due to the reduced pressure does not disappear, since an existence of the air within the chamber is maintained in spite of the deformation of the alveolar gingiva.

Figure 8:
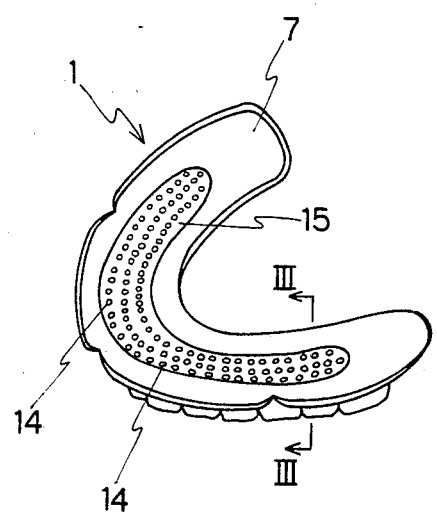
FIG. 8 is a perspective view from the bottom showing a second embodiment of a dental prosthesis of the present invention.
Figure 9:
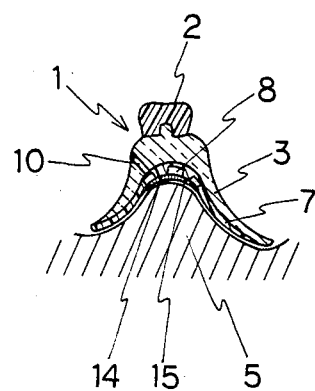
FIG. 9 is a sectional view taken along line III—III of FIG. 8.

FIGS. 8 and 9 show a second embodiment of the dental prosthesis of the present invention. In such an embodiment, the recess portion 8 is covered with a plate member 15 having a number of small apertures. Preferably, the plate member 15 is not deformed, if the plate member receives a pushing force of the alveolus ridge or a sucking force generated within the chamber of the recess portion 8. The plate member 15 may be flexible like a spring so as to return to the original shape, even if the plate member 15 is deformed. Such a plate member 15 may be made of a mesh of metal sheet, a porous metal plate, a mesh of synthetic resin, a sheet of synthetic resin, a sheet of rubber, and the like. The plate member 15 may be integrally provided with the above projections 9, so that the alveolar gingiva can be more surely prevented from projecting into the recess portion 8. The plate member 15 may be incorporated so as to be detachable.

In the first and second embodiments, the dental prosthesis is provide with a proper number of small bores 10. The exits of the small bores 10 may be located near both ends of the denture base 3.

In operation of such a dental prosthesis, the elastic lining layer 7 is compressed by the pressure applied to the dental prosthesis 1 during mastication movement. At the same time, the chamber of the recess portion 8 is also compressed. As a result, the air in the sealed chamber is partially exhausted to an exterior through the small bore 10 and the check valve 11. Then, when the pressure applied to the dental prosthesis 1 is removed, the elastic lining layer 7 is return to the original shape and a volume of the sealed chamber of the recess portion 8 is increased, which makes the pressure in the sealed chamber reduced. Consequently, the dental prosthesis 1 is fixed to the alveolus ridge 5 by the strong sucking force. In such a way, since the operation of exhausting the air through the small bore 10 is effected at every mastication movement, the sucking force is maintained or increased, and thus the strong fixing force can be obtained.

The dental prosthesis descirbed in the above embodiments is used as a dental prosthesis of the alveolar part of mandible. However, the structure of such a dental prosthesis can be also used as a dental prosthesis of the maxillae or as a partial dental prosthesis.

When the height of the alveolus ridge is uneven along the alveolus ridge, it is difficult that enough recess portion is provided on the inner surface of the denture base, since a thickness of the denture base corresponding to the projecting part of the alveolus ridge becomes thin. In that case, the recess may be provided on parts of the inner surface of the denture base which corresponds to concaves of the alveolus ridge. When the recesses are formed individually, the recesses are preferably communicated with each other through a narrow channel so that the inner pressures of the sealed chamber of the recesses are equal to each other.

According to the present invention, when the chamber between the alveolus ridge and the recess portion provided on the inner surface of the dental base is compressed during mastication movement, the air in the sealed chamber is exhausted to an exterior through the small bore and the check valve. Then, when the pressure is removed, the pressure in the sealed chamber is reduced. As a result, the sucking force of the dental prosthesis against the alveolus ridge is much increased. Further, since the recess is provided with a member preventing the alveolar gingiva from projecting into the recess, i.e. a number of projections and/or a plate member, there is no fear that the alveolar gingiva projects into the recess. Therefore, the stable sucking force can be effectively maintained for a long time.

Further, according to the present invention, since the inner surface of the denture base has the elastic lining layer, the elastic lining layer is compressed a little by the pressure applied to the dental prosthesis during mastication movement. As a result, the volume of the sealed chamber of the recess portion is largely increased or decreased, which can produce a larger sucking force. This effects are advantageous for a dental prosthesis to be engaged with the maxillae, which is generally provide with a covering plate which covers all over the surface of the maxillae. According to the present invention it is not necessary to provide the covering plate, because there is no fear that the dental prosthesis comes off or falls off during mastication movement or by its own weight due to the strong sucking force. Therefore, uncomfortable feeling due to the covering plate can be avoided.

Further, in case that the dental prosthesis of the invention is adapted to a partial dental prosthesis, it is not necessary, due to the strengthened sucking force, to provide a clasp. Accordingly, though a conventional partial dental prosthesis having a clasp often gives a damage to teeth which are adjacent to the partial dental prosthesis, there is no damage to the teeth and the appearance of the teeth becomes excellent.

Generally, alveolus ridges and jaws are changed in shapes due to recession, and a fitness between the alveolus ridge and the denture base becomes worse. If the dental prosthesis continues to be used under such an unfitted condition, the deformation of the alveolus ridge due to the recession is more and more promoted, and then the dental prosthesis must be wholly prepared again. With respect to the problem, according to the present invention, the deformation due to the recession is restrained to the minimum, since the dental prosthesis is stably sucked. Therefore, the fitness of the dental prosthesis can be maintained for a long period. Further, according to the present invention, even if the alveolus ridge is deformed a little, only an elastic lining layer is peeled off from the dental prosthesis and a new elastic lining layer impressed again can be fixed on the inner surface of the denture base. Therefore, almost parts of the dental prosthesis can be used as they are, which can reduce cost.

In the present invention, it is preferable to employ a thermosetting (crosslinkable) polymer as a material of the denture base, and a thermoplastic elastomer as the elastic lining layer.

When using the materials of different kinds, it should be noted that the elastic lining layer is readily peeled off from the denture base unless the fixing between them is enough.

According to the present invention, strong fixing can be accomplished by using materials having substantially the same value of solubility parameter (hereinafter referred to as "SP value"). The words "materials having substantially the same SP value" means that an SP value of one material is within a range of ±15% of the SP value of the other material.

When the SP values of two polymer materials are substantially the same, the two polymer materials can be readily fused together because of good compalibility therebetween. For instance, when using a thermoplastic urethane elastomer (SP value: 10.0) as the elastic lining layer, it is preferable to employ polymethylmethacrylate (SP value: 9.3 to 9.9) as the denture base. Examples of the material for the denture base other than polymethylmethacrylate which are compatible with the thermoplastic urethane elastomer are, for instance, polyethersulfone (SP value: 9.7 to 9.9), polysulfone (SP value: 9.9), polycarbonate (SP value: 9.8), and the like.

A process for preparing a dental prosthesis of the present invention, for example the step, comprises (1) forming a mouth model corresponding to a profile of an alveolus ridge of a patient with gypsum in a first flask;
(2) forming a denture base of a hard polymer material with gypsum in a second flask, the denture base being concaved by a predetermined thickness at an inner surface portion of the denture base;
(3) attaching a spacer having a predetermined shape on the top of the mouth model;
(4) coupling the first and second flask to form a space between the denture base and the mouth model, and filling a thermoplastic elastomer in a semi-fluidized state into the space, the thermoplastic elastomer being compatible with the hard polymer material;
(5) separating the first flask and the second flask after the thermoplastic elastomer is cooled to form an elastic lining layer, and removing the spacer to form a recess portion in the elastic lining layer;
(6) forming a small bore which penetrates from the recess portion to an outer surface of the denture base; and
(7) providing a valve member within the small bore.

The step (1) can be performed by employing a conventional method as it is. That is, a female die of an alveolus ridge of a patient is formed with a room temperature thermosetting resin, and then, a plastic material such as gypsum is casted into the female die and hardened to form a mouth model having a shape of an inverted approximate U-shape.

The step (2) is a step for forming the denture base having a space for the elastic lining layer. The step can be performed according to the following procedures shown in FIGS. 10A to 10J.

Figure 10A:
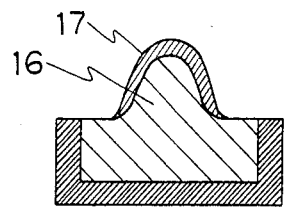
FIGS. 10A to 10J are diagrams showing procedures of step (2) of the process according to the present invention.

Procedure in FIG. 10A

An elastic lining layer model 17 having the same profile as that of the elastic lining layer is put on the mouth model 16 formed in the step (1). The elastic lining layer model 17 is made of a sheet of metal such as lead, a sheet of synthetic resin, or the like having a good plasticity and processablility.

Figure 10B:
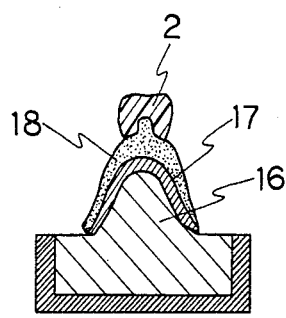

Procedure in FIG. 10B

A wax is applied to the elastic lining layer model 17 on the mouth model to 16 form a temporary denture base 18. Then, artificial teeth 2 are embedded in the temporary denture base 18.

Figure 10C:
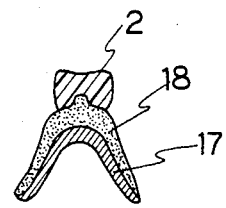

Procedure in FIG. 10C

The temporary denture base 18 with the elastic lining layer model 17 and the artificial teeth 2 is detached from the mouth model 16, and then the temporary denture base is engaged with the alveolus ridge of the patient to test a fitting property. On the basis of the test results, an arrangement of the artificial teeth 2 or a profile of the temporary denture base 18 is adjusted.

Figure 10D:
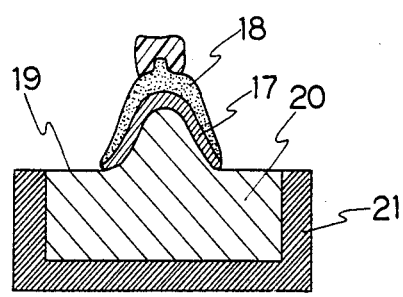

Procedure in FIG. 10D

The temporary denture base 18 having the artificial teeth 2 and the elastic lining layer model 17 is put in a first flask 21 filled with a liquid gypsum, and then the inner surface of the elastic lining layer model 17 is fitted to the gypsum. After the gypsum 20 is solidified, a surface 19 of the gypsum 20 is coated with a mold-release agent such as an aqueous solution of a soap.

Figure 10E:
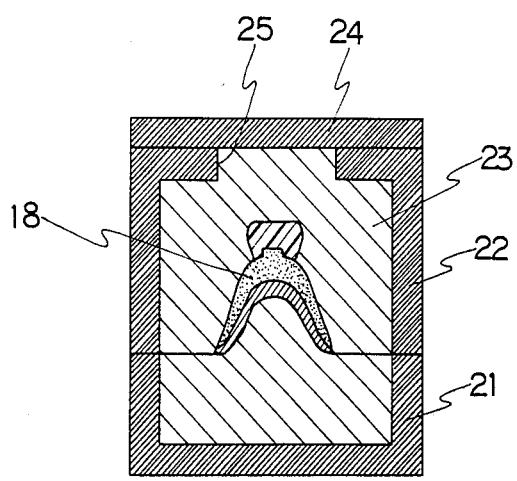

Procedure in FIG. 10E

A second flask 22 is put on the first flask 21. A liquid gypsum 23 is introduced into the interior of the second flask 22 through an opening 25 provided on a top of the second flask 22, and the gypsum 23 is compressed by a lid 24, and then the opening 25 is closed by the lid 24. After the gypsum 23 is solidified, all flasks are dipped into hot water in the fixed state for about five minutes, so that the temporary denture base 18 made of wax is softened and melted.

Figure 10F:
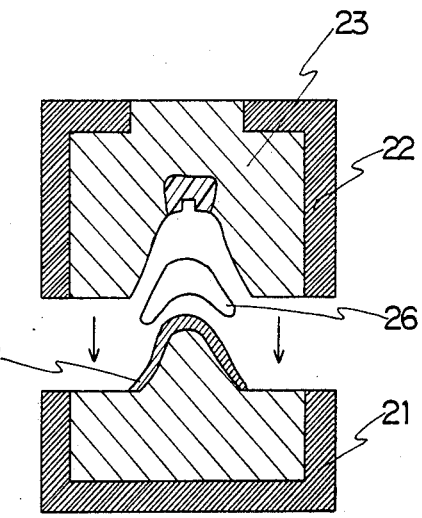

Procedure in FIG. 10F

The first flask 21 and the second flask 22 are separated from each other, and the molten wax is removed. After a surface of the gypsum 23 is coated with a mold-release agent, the space corresponding to the denture base is filled with a synthetic resin being in a state like a rice cake, such as polymethylmethacrylate 26.

Figure 10G:
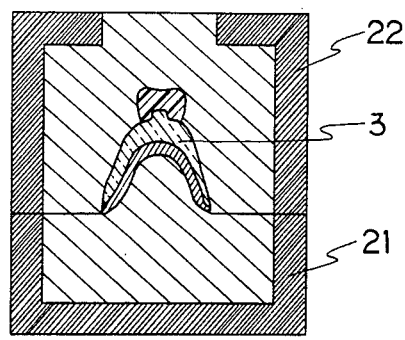

Procedure in FIG. 10G

The first flask 21 and the second flask 22 are compressed to each other, and are dipped into hot water for about one hour, so that the polymethylmethacrylate 26 is hardened to form a denture base 3.

Figure 10I:
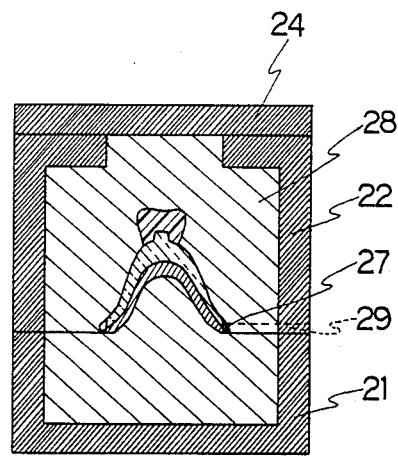
Figure 10H:
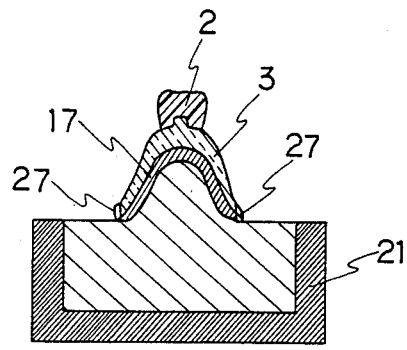

Procedure in FIG. 10H

After cooling, the second flask 22 is separated. After a surface of the denture base 3 is polished, a lower portion of the denture base 3 where the elastic lining layer model 17 comes out is coated with a wax 27. The wax 27 covers the edges of the lower end of the denture base 3 a little and seals a boundary line between the denture base 3 and the surface of the gypsum. The surface of the gypsum is coated with a mold-release agent.

Procedure in FIG. 10I

The second flask 22 is put on the first flask 21. A liquid gypsum 28 is introduced into the second flask 22 from an opening provided on a top of the second flask 22. After the gypsum 28 is compressed by the lid 24, the opening is closed by the lid 24. At the same time, a narrow channel 29 which communicates the wax 27 with an exterior is formed.

Figure 10J:
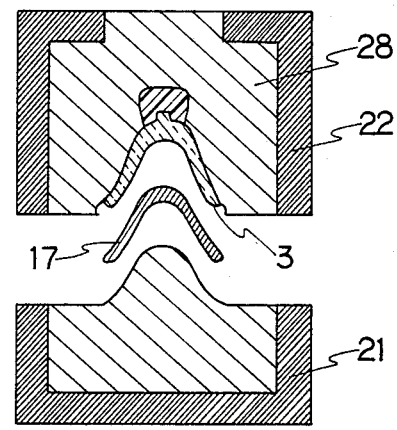

Procedure in FIG. 10J

After the gypsum 28 is solidified, the flasks are dipped into hot water. Then, the first flask 21 and the second flask 22 are separated from each other, and the wax 27 is removed. After the flasks are taken out from hot water, the elastic lining layer model 17 is detached from the denture base 3. An inner surface of the denture base 3 is cleaned by polishing.

In this way, the denture base in the present invention is obtained.

The denture base can be also formed by means of employing a wax instead of the elastic lining layer model 17. FIGS. 11A to 11I show procedures of such a method.

Figure 11A:
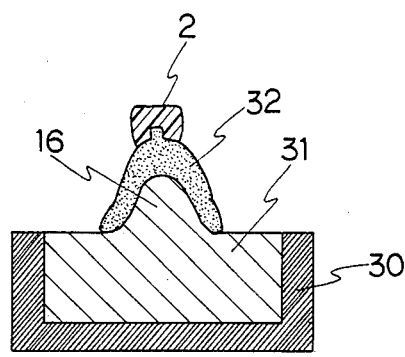

Procedure in FIG. 11A

An interior of a first flask 30 is filled with a liquid gypsum 31 to form a mouth model 16. After the gypsum 31 is solidified, a wax pattern 32 having a shape of a denture base is put on the mouth model 16. Artificial teeth 2 are arranged on the wax pattern 32.

Figure 11C:
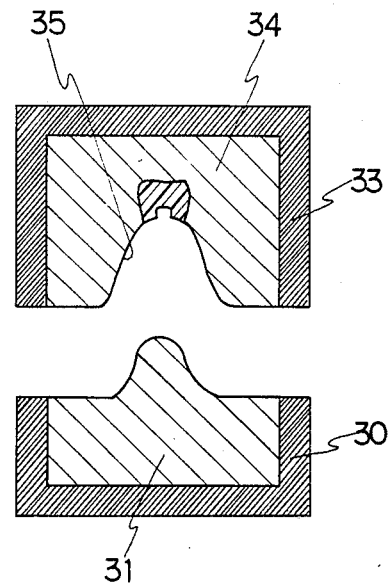
Figure 11B:
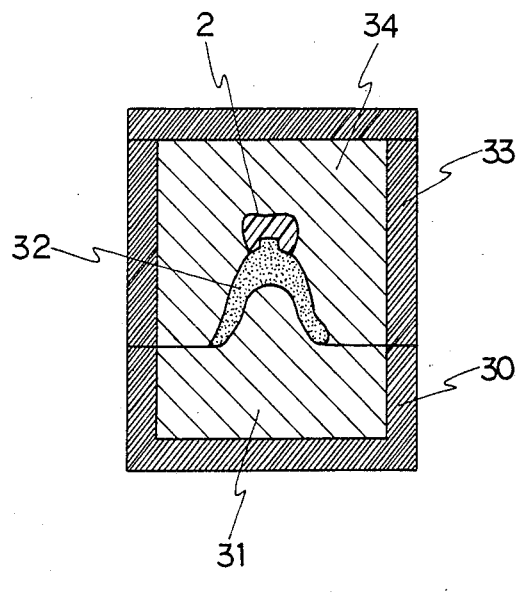

Procedure in FIG. 11B

A second flask 33 is put on the first flask 30. A liquid gypsum 34 is introduced into an interior of the second flask 33.

Procedure in FIG. 11C

After the gypsum 34 is solidified, the flasks are dipped into hot water so that the wax pattern 32 is melted and removed. In this state, the artificial teeth 2 are buried in the gypsum 34 and a concave portion 35 corresponding to a profile of a surface of a denture base is formed.

Figure 11D:
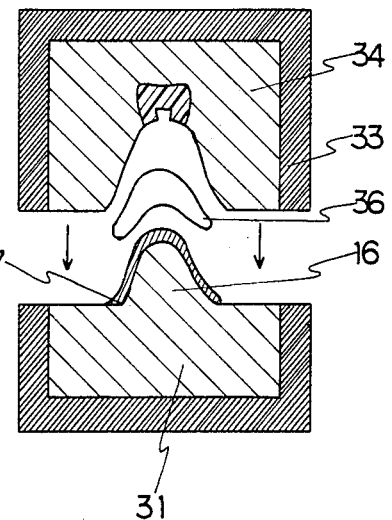

Procedure in FIG. 11D

The concave portion 35 is filled with a proper amount of clay 36. On the other hand, a predetermined thickness (about 0.5 mm) of a wax pattern 37 is formed on a surface of the mouth model 16.

Procedure in FIG. 11E

The first flask 30 with the gypsum 31 and the second flask 33 with the gypsum 34 are compressed with each other, so that the clay is molded into a shape of the denture base excepting a part of the wax pattern 37.

Procedure in FIG. 11F

After that, the flasks are dipped into hot water and separated to each other, so that the wax pattern 37 is melted and removed.

Procedure in FIG. 11G

The first flask 33 is reversed to the lower position. Another second flask 38 is put on the first flask 33, and an interior of the second flask 38 is filled with a liquid gypsum 39 to form another mouth model 40 having a profile which includes the wax pattern 37 in addition to the mouth model 16. After the gypsum 39 is solidified, the flasks 33 and 38 are separated from each other, and then the clay 36 is removed.

Procedure in FIG. 11H

A polymethylmethacrylate resin 41 in a state like a rice cake is filled into the concave portion 35. The polymethylmethacrylate resin is produced by mixing polymethylmethacrylate powder containing a crosslinking agent with liquid methylmethacrylate monomer.

Procedure in FIG. 11I

The flasks 33 and 38 are dipped into hot water (about 100° C.) for about thirty minutes in a state that the flasks 33 and 38 are compressed to each other. As a result, the polymethylmethacrylate 41 is crosslinked and hardened, so that the denture base 3 is formed. At the same time, the artificial teeth 2 are held on the denture base 3.

The step (3) in the process of the present invention is a step where a spacer 42 is attached on the top of the mouth mold 16. The spacer 42 is a die for forming the recess portion 8 and the projections 9 in the elastic lining layer 7 provided on the inner surface of the denture base 3. FIG. 12 shows the procedure in the step (3). The spacer 42 is a sheet of metal which is thined at its periphery and provided with a number of small holes.

The step (4) is a step for forming the elastic lining layer 7. FIG. 13 shows a procedure in the step (4). The flask 22 having the denture base 3 is put on the flask 21 having the mouth mold 16 on which the spacer 42 is fixed. Subsequently, an elastic material such as a thermoplastic urethane elastomer is introduced into the space which has a shape of the elastic lining layer model 17 through the narrow 29. When the molten thermoplastic elastomer is in contact with the inner surface of the denture base 3, the contacting surface of the inner surface of the denture base 3 is melted. In such a state, the fluidized polymer molecules of the denture base and the molecules of the thermoplastic elastomer are tanged with each other to the extend that the boundary surface cannot be distinguished. As a result, strong bond between the elastic lining layer 7 and the denture base 3 is obtained in an integral form.

A press molding method can be employed instead of the above casting method. FIGS. 14A and 14B show such procedures. As shown in FIG. 14A, a thermoplastic urethane elastomer sheet 43 whose thickness is about 0.5 to 1.5 mm is put on the spacer 42 attached to the mouth mold 16. Hot air is blown against the sheet 43 from a hot air outlet 45, so that the sheet 43 is softened and fluidized. Alternatively, the flask 22 may be positioned at the lower side, the thermoplastic urethane elastomer sheet 43 is put on the inner surface of the denture base 3, and then the sheet 43 is heated. Subsequently, by pressing the flask 22 to the flask 21 as shown in FIG. 14B, the molten thermoplastic urethane elastomer sheet 43 is compressed.

When the operations in the step (4) are carried out under an atmospheric environment, air bubbles are sometimes formed. To resolve such a problem, all operations in the step (4) are carried out under a reduced pressure. In that case, an infrared heater is preferably employed to heat the sheet 43.

In the step (5), after the elastic lining layer 7 is solidified, the flasks 21 and 22 are separated from each other. The gypsums 20 and 28 are broken into pieces, and the dental prosthesis is taken out. At the same time, the spacer 30 is removed. As a result, a recess portion 8 having a number of the projections 9 is formed on the inner surface of the elastic lining layer 7.

In the dental prosthesis of the present invention, the check valve member 11 communicating the recess portion 8 with the exterior of the denture base 3 is formed in the step (6) and the step (7).

As shown in FIG. 7, after the small bore 10 is prepared by penetrating from the recess portion 8 of the elastic lining layer 7 to the outer surface of the denture base 3, the check valve 11 is inserted.

According to the above steps, the dental prosthesis of the present invention can be completely prepared.

In the embodiments described above, though the elastic lining layer and the denture base are fixed without any adhesive, the elastic lining layer can also be fixed with an adhesive.

As the adhesive, it is preferable to employ a solution prepared by dissolving the same polymer material as that of the denture base in a solvent having substantially the same SP value as the denture base material. The solvent has also substantially the same SP value as the thermoplastic elastomer. For instance, when using polymethylmethacrylate as the denture base material and a thermoplastic urethane elastomer as the elastic lining layer material, strong adhesion strength can be obtained by using a solution of polymethylmethacrylate in tetrahydrofuran (SP value: 9.9) as the adhesive. In that case, the non-crosslinked polymethylmethacrylate polymer chains in the adhesive enter into the surface portion of the crosslinked polymethylmethacrylate matrix of the denture base and tangle therewith to give an integral structure. The thermoplastic urethane elastomer is also fused together with the non-crosslinked polymethylmethacrylate to form an integral structure when cooled and hardened. Accordingly, the elastic lining layer is strongly adhered and fixed to the denture base via the adhesive.

Examples of the solvent for the adhesive of polymethylmethacrylate are, for instance, n-methylpyrrolidone (SP: 9.8), cyclohexane (SP: 9.9), metyl ethyl ketone (SP: 9.3), diethyl ketone (SP: 8.8), acetone (SP: 10.0), dichloromethane (SP: 9.7), chloroform (SP: 9.3), dichloroethane (SP: 9.8), tetrachloroethane (SP: 10.4), bromobenzene (SP: 10.0), bromotoluene (SP: 9.8), bromoform (SP: 10.5), dibromoethane (SP: 10.4), tribromopropane (SP: 10.7), methyl iodide (SP: 9.9), ethyl iodide (SP: 9.4), n-heptanol (SP: 10.0), n-octanol (SP: 10.3), n-hexanol (SP: 10.7), methyl formate (SP: 10.7), ethyl formate (SP: 9.4), methyl acetate (SP: 9.6), ethyl acetate (SP: 9.1), diethyl malonate (SP: 10.3), ethyl benzoate (SP: 9.7), diethyl phthalate (SP: 10.05), n-butyl acrylate (SP: 8.9), benzaldehyde (SP: 10.8), acetaldehyde (SP: 9.8), n-heptaldehyde (SP: 9.7), methyl n-propyl ketone (SP: 8.7), methyl n-butyl ketone (SP: 8.6), dioxane (SP: 10.0), aniline (SP: 10.8), pyridine (SP: 10.7), propionitrile (SP: 10.7), n-butyronitrile (SP: 10.5), n-valeronitrile (SP: 10.1), capronitrile (SP: 10.2), methacrylonitrile (SP: 9.1), 2-nitropropane (SP: 9.9), nitrobenzene (SP: 10.0), o-nitrotoluene (SP: 10.5), m-nitrotoluene (SP: 10.4), carbon disulfide (SP: 10.0), dimethyl sulfide (SP: 9.0), thiophene (SP: 9.8), benzene (SP: 9.15), an admixture thereof, and the like.

In case that the adhesive is employed, a step for applying the adhesive to the inner surface of the denture base and drying the adhesive is added after the step (2), i.e. the step of preparation of the denture base.

According to the process of the present invention, the strength between the denture base and the elastic lining layer can be increased in comparison with strength in a conventional structure where the elastic lining layer is adhered to the denture base via a commercially available adhesive. That is to say, the fixing strength is approximately equal to the strength of the elastic lining layer according to the present invention. Such a fixing strength can be obtained by the fact that the polymer molecules in the denture base and the polymer molecules of the elastic lining layer are tangled with each other at the fixing area.

Further, according to the process of the present invention, the thickness of the denture base can be reduced in comparison with a conventional dental prosthesis where mechanical engagement is employed between the denture base and the elastic lining layer. Therefore, the dental prosthesis of the present invention can reduce uncomfortable feeling.

What we claim is:

1. A dental prosthesis having artificial teeth, a denture base of hard polymer material holding said artificial teeth and an elastic lining layer substantially covering the inner surface of said denture base, comprising:
    (a) a recess portion of the same material as the material of said elastic lining layer on said elastic lining layer for forming a sealed chamber defined by said elastic lining layer and the mucosa of the alveolus ridge of the wearer of said dental prosthesis;
    (b) a small bore for communicating said sealed chamber with the exterior of said dental prosthesis through said elastic lining layer and said denture base;
    (c) a check valve of a soft elastic material in said small bore near the exit end of said small bore for exhausting air in said chamber from said recess portion to said exterior, said check valve having a triangle section projection from said exit end in the direction toward the interior of said base; and
    (d) a member for preventing the alveloar gingiva of said wearer of said dental prosthesis from projecting into said recess portion due to a deformation of said wearer's alveolar gingiva, said preventing member including a number of projections of the same material as that of said elastic lining layer, said projections being located within said recess portion, each projection having a height no greater than the distance between the bottom of said recess portion and said mucosa of the alveolus ridge of said wearer.

2. The dental prosthesis of claim 1, wherein said member for preventing the alveolar gingiva from projecting has a plate covering said recess portion, said plate having a number of small apertures and having a profile corresponding to that of said mucosa of the alveolus ridge of said wearer.

3. The dental prosthesis of claim 1, wherein said hard polymer material is selected from the group consisting of polymethylmethacrylate, polyethersulfone, polysulfone and polycarbonate, and said elastic lining layer is made of a thermoplastic elastomer compatible with said hard polymer material.

4. The dental prosthesis of claim 3, wherein said thermoplastic elastomer is a thermoplastic urethane elastomer.

5. A process for preparing a dental prosthesis, the steps comprising
   (1) forming a mouth model corresponding to a profile of the alveolus ridge of the patient with gypsum in a first flask;
   (2) forming a denture base of a hard polymer material with gypsum in a second flask, said denture base being concaved by a predetermined thickness at an inner surface portion of said denture base;
   (3) attaching a spacer having a predetermined shape on the top of said mouth model;
   (4) coupling said first and second flask to form a space between said denture base and said mouth model, and filling a thermoplastic elastomer in a semi-fluidized state into said space, said thermoplastic elastomer being compatible with said hard polymer material;
   (5) separating said first flask and said second flask after said thermoplastic elastomer is cooled to form an elastic lining layer substantially covering the inner surface of said denture base, and removing said spacer to form a recess portion in said elastic lining layer;
   (6) forming a small bore which penetrates from said recess portion to an outer surface of the denture base; and
   (7) providing a valve member within the small bore.

6. A process for preparing a dental prosthesis, the steps comprising
   (1) forming a mouth model corresponding to a profile of the alveolus ridge of the patient with gypsum in a first flask;
   (2) forming a denture base of a hard polymer material with gypsum in a second flask, said denture base being concaved by a predetermined thickness at an inner surface of the denture base;
   (3) applying an adhesive to the inner surface of said denture base and drying the adhesive, said adhesive being prepared by dissolving the hard polymer material in a solvent which is compatible with the hard polymer material;
   (4) attaching a spacer having a predetermined shape on the top of the mouth model;
   (5) coupling said first and second flasks to form a space between said denture base and said mouth model, and filling a thermoplastic elastomer in a semi-fluidized state into said space, said thermoplastic elastomer being compatible with said hard polymer material;
   (6) separating said first flask and said second flask after said thermoplastic elastomer is cooled to form an elastic lining layer substantially covering the inner surface of said denture base, and removing said spacer to form a recess portion in the elastic lining layer;
   (7) forming a small bore which penetrates from said recess portion to an outer surface of the denture base; and
   (8) providing a valve member within said small bore.

* * * * *